(12) United States Patent
Daxer

(10) Patent No.: US 8,092,526 B2
(45) Date of Patent: Jan. 10, 2012

(54) CORNEA IMPLANT

(76) Inventor: Albert Daxer, Linz (AT)

( * ) Notice: Subject to any disclaimer, the term of this patent is extended or adjusted under 35 U.S.C. 154(b) by 0 days.

(21) Appl. No.: 12/224,966

(22) PCT Filed: Mar. 16, 2007

(86) PCT No.: PCT/AT2007/000130
§ 371 (c)(1),
(2), (4) Date: Sep. 9, 2008

(87) PCT Pub. No.: WO2007/104068
PCT Pub. Date: Sep. 20, 2007

(65) Prior Publication Data
US 2009/0076601 A1    Mar. 19, 2009

(30) Foreign Application Priority Data
Mar. 16, 2006 (AT) .................................. A428/2006

(51) Int. Cl.
*A61F 2/14* (2006.01)
(52) U.S. Cl. ..................................... 623/5.16; 623/5.12
(58) Field of Classification Search ................... 623/4.1, 623/5.13, 5.11–5.16
See application file for complete search history.

(56) References Cited

U.S. PATENT DOCUMENTS

| | | | |
|---|---|---|---|
| 4,662,370 A | 5/1987 | Hoffmann et al. |
| 5,215,104 A | 6/1993 | Steinert |
| 5,342,378 A | 8/1994 | Giraud et al. |
| 5,549,632 A | 8/1996 | Lai |
| 5,556,406 A | 9/1996 | Gordon et al. |
| 5,624,456 A | 4/1997 | Hellenkamp |
| 5,722,971 A | 3/1998 | Peyman |
| 5,817,115 A | 10/1998 | Nigam |
| 5,964,776 A | 10/1999 | Peyman |
| 6,056,764 A | 5/2000 | Smith |
| 6,083,236 A | 7/2000 | Feingold |
| 6,126,668 A | 10/2000 | Bair et al. |
| 6,132,446 A | 10/2000 | Hellenkamp et al. |
| 6,139,559 A | 10/2000 | Nordan et al. |

(Continued)

FOREIGN PATENT DOCUMENTS
DE          34 33 581          3/1986
(Continued)

OTHER PUBLICATIONS
International Search Report.
(Continued)

*Primary Examiner* — David H Willse
*Assistant Examiner* — Javier Blanco
(74) *Attorney, Agent, or Firm* — Collard & Roe, P.C.

(57) ABSTRACT

Annular cornea implant for inserting into a cornea pocket of the human eye via a narrow, tunnel-shaped access, with the end shape of the cornea implant depending on the shortsightedness or astigmatism to be corrected. The aim of the invention is to enable the cornea implant to be implanted in the cornea pocket in a simple manner and in an optimum position. To this end, the implant has a shape memory which is impressed on the basis of the geometry and/or material of the implant, and is designed in such a way that the deformability from a starting shape enables the insertion of the cornea implant into the cornea pocket via the narrow access, and the cornea implant has an adjustment force in the end shape thereof, which enables an essentially independent unfolding of the cornea implant in the cornea pocket.

19 Claims, 9 Drawing Sheets

U.S. PATENT DOCUMENTS

Figure 1:
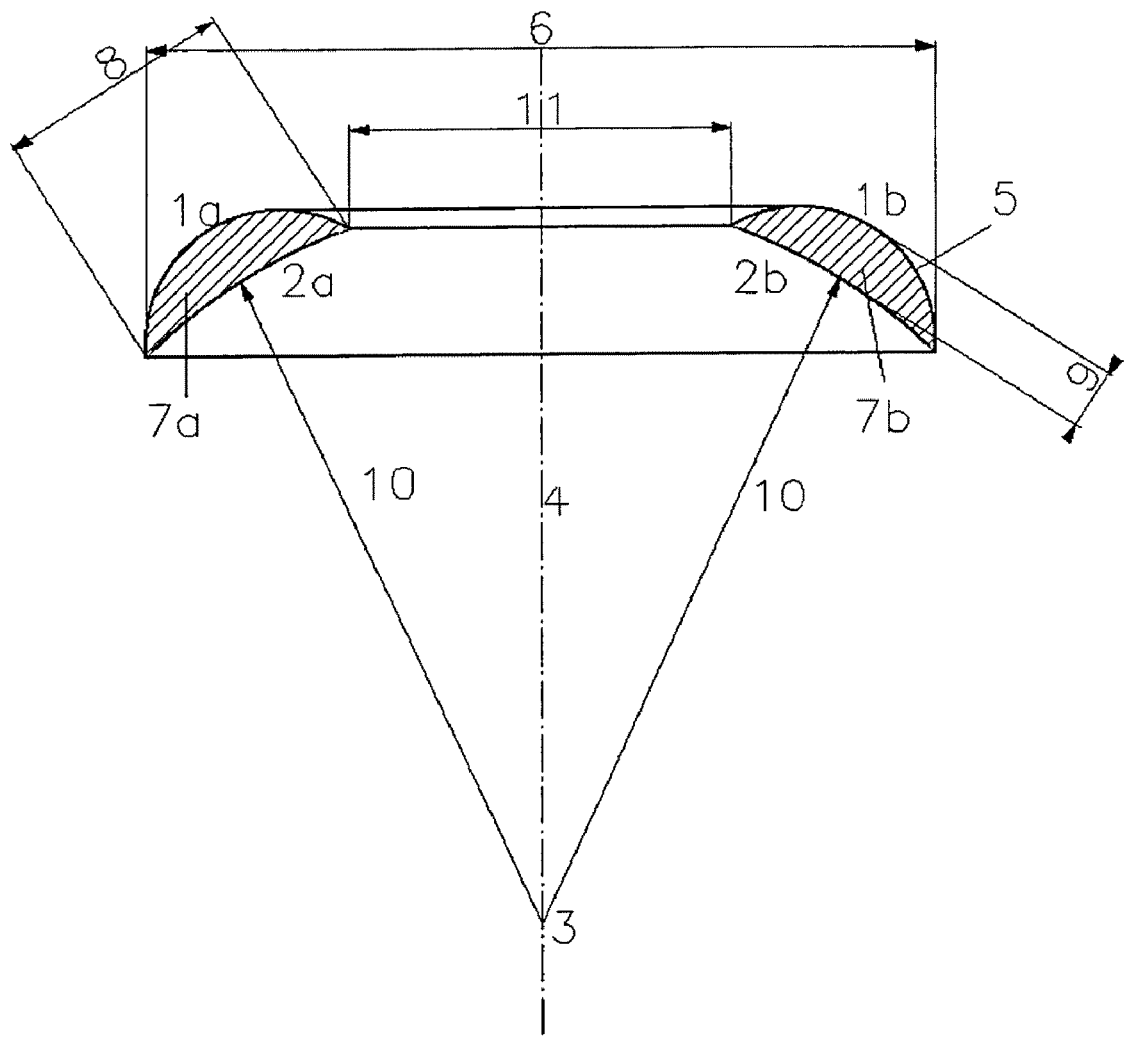

| | | | |
|---|---|---|---|
| 6,228,114 B1 * | 5/2001 | Lee | 623/5.12 |
| 6,312,440 B1 | 11/2001 | Hood et al. | |
| 6,358,262 B1 | 3/2002 | Chan et al. | |
| 6,428,572 B2 * | 8/2002 | Nagai | 623/4.1 |
| 6,506,198 B1 | 1/2003 | Amano | |
| 6,543,453 B1 * | 4/2003 | Klima et al. | 128/898 |
| 6,589,280 B1 | 7/2003 | Koziol | |
| 6,599,305 B1 | 7/2003 | Feingold | |
| 6,615,496 B1 | 9/2003 | Fleming et al. | |
| 6,679,605 B2 * | 1/2004 | Zhou et al. | 351/159 |
| 6,923,821 B2 | 8/2005 | Wortrich | |
| 2001/0004702 A1 | 6/2001 | Peyman | |
| 2001/0004708 A1 | 6/2001 | Nagai | |
| 2001/0027314 A1 | 10/2001 | Peyman | |
| 2002/0013622 A1 * | 1/2002 | Hennig | 623/5.12 |
| 2002/0055753 A1 | 5/2002 | Silvestrini | |
| 2003/0033015 A1 | 2/2003 | Zhou et al. | |
| 2004/0073303 A1 | 4/2004 | Schanzlin et al. | |
| 2004/0143324 A1 | 7/2004 | Melles | |
| 2004/0260320 A1 | 12/2004 | Lisk et al. | |
| 2005/0080484 A1 * | 4/2005 | Marmo et al. | 623/5.14 |
| 2005/0119738 A1 | 6/2005 | Nigam | |
| 2006/0036318 A1 | 2/2006 | Foulkes | |
| 2006/0116759 A1 | 6/2006 | Thornton et al. | |
| 2006/0235513 A1 * | 10/2006 | Price | 623/5.12 |
| 2007/0016234 A1 | 1/2007 | Daxer | |
| 2009/0240327 A1 | 9/2009 | Daxer | |

FOREIGN PATENT DOCUMENTS

| | | |
|---|---|---|
| EP | 1 364 633 | 11/2003 |
| EP | 1 620 049 | 2/2006 |
| GB | 2 095 119 | 9/1982 |
| WO | WO 93/05731 | 4/1993 |
| WO | WO 93/12735 | 7/1993 |
| WO | WO 93/14703 | 8/1993 |
| WO | WO 01/15779 | 3/2001 |
| WO | WO 01/49334 | 7/2001 |
| WO | WO 02/06883 | 1/2002 |
| WO | WO 03/001965 | 1/2003 |
| WO | WO 03/015674 | 2/2003 |
| WO | WO 03/020176 | 3/2003 |
| WO | WO 03/020190 | 3/2003 |
| WO | WO 2004/096106 | 11/2004 |
| WO | WO 2005/082265 | 9/2005 |

OTHER PUBLICATIONS

International Search Report of PCT/EP2010/052123, dated Jun. 11, 2010.

International Search Report in PCT/EP2007/055015, dated Sep. 13, 2007.

International Search Report in PCT/AT2004/000147, dated Aug. 31, 2004.

Eisner, "Eye Surgery: An Introduction to Operative Technique" Springer-Verlag Berlin Heidelberg 1978, pp. 67-69.

Daxer A. et al., "Collagen Fibrils in the Human Corneal Stroma: Structure and Aging," Invest. Opthalmol & Vis. Sci, Mar. 1998, vol. 39, No. 3, pp. 644-648.

Spoerl E, Huhle M, Seiler T., "Induction of cross-links in corneal tissue", Abstract Exp. Eye Res., Jan. 1998; 66(1):97-103; 1 page.

* cited by examiner

CORNEA IMPLANT

CROSS REFERENCE TO RELATED APPLICATIONS

This application is the National Stage of PCT/AT2007/000130 filed on Mar. 16, 2007, which claims priority under 35 U.S.C. §119 of Austrian Application No. A 428/2006 filed on Mar. 16, 2006. The international application under PCT article 21(2) was not published in English.

AREA OF THE INVENTION

The present invention relates to an annular cornea implant for inserting into a cornea pocket of the human eye via a narrow, preferably tunnel-shaped access, with the end shape of the cornea implant depending on the refractive error to be corrected.

STATE OF THE ART

The optical apparatus of the human eye for depicting the environment basically consists of the cornea and the lens which is positioned behind the iris. This optical apparatus of the eye has a total refractive power of approximately 60 dioptres, with the interface between the cornea and the air—i.e. the outer boundary of the eye—with approximately 40 dioptres accounting for most of the refractive power. This refractive power of the cornea is basically indirectly proportionate to the radius of the cornea surface (interface between cornea and air). A change in the radius of the curvature of the cornea also leads to a change in the refractive power of the eye. By increasing the (central) radius of curvature of the cornea the refractive power decreases, a fact which the eye surgeon takes advantage of in refractive surgery for the correction of shortsightedness. The refractive surgical techniques using laser (LASIK, LASEK, etc.) remove more corneal tissue from the central parts than from the peripheral parts of the cornea.

With the LASIK technique, for instance, a lamellar "flap" is cut into the cornea at a certain depth. Such flaps have the major disadvantage that they significantly impair the biomechanical stability of the cornea. The flap, in particular, no longer fully adheres to the underlying corneal tissue. This reduces the bio-mechanically effective cross section of the cornea by exactly the amount that corresponds to the thickness of the flap. The preferable option would be to undertake corrective measures on the inside of the cornea, without risking such a massive biomechanical impairment as is caused by a flap. Moreover, the laser techniques mentioned above are only suited for the treatment of myopic patients with up to 10 dioptres.

To avoid these drawbacks, methods have been developed in which cornea implants are used that cause a deformation of the cornea to the effect that the radius of curvature of the cornea is enhanced by adding volume, which in turn reduces the refractive power and thus corrects the myopic eye.

Cornea implants are mostly annular or ring-shaped, using either full rings (open or closed) or parted rings (e.g. ring segments).

US 2005/0119738 A1, for example, reports the use of such a cornea implant underneath a flap. It describes an annular implant for insertion into the cornea underneath a flap. In this case, a central part of the cornea implant is directly optically effective, i.e. in order to fulfill its task, it must be part of the optical zone and be penetrated by the rays of light to be depicted. The cornea implant has the task to form a multifocal corneal surface, with the area of the central hole in the cornea implant being responsible for near vision and the area that also includes the inner part of the cornea implant (optical zone) for far vision. To be able to solve this difficult task, the optical zone (including the inner part of the cornea implant) must be located within the diameter of the pupil of the eye, which is mostly 2 to 5 mm. The inner hole of the cornea implant therefore must not be essentially larger than 2 mm. Moreover, the inner part of the cornea implant, which is intended to be directly involved in producing an image in far vision, must have a minimum width which, taking account of the optical laws, must substantially exceed 1 mm (2 mm) in order to be effective. Added to this is the outer part of the cornea implant. This results in the substantial problem that the significant material width, which by far exceeds 1 mm, may lead to problems with oxygen and nutrient supply. While the problem with nutrient supply may be ameliorated by using the microporous hydrogel indicated, problems with stability and stabilisation of the ring geometry still tend to arise due to the softness of the ring.

Moreover, the cornea implant has no pointed end on its inner or outer edge, but a finite edge thickness of preferably 10 μm. These edges have the considerable disadvantage that deposits may occur in the area, leading to vision impairment.

Experience with multifocal imaging, both in contact lens adjustment and in the implantation of intraocular lenses in cataract surgery, shows that this is tolerated by only a small minority of patients. The majority of patients perceive the simultaneous "blur" of the focal point along the optical axis as disturbing rather than beneficial. Moreover, it is to be expected that with respect to the present structure, patients will perceive the central part of the cornea implant, and here in particular the inner edge that needs to lie within the pupil width, as disturbing (despite adjustment to the refractive index of the surrounding medium).

As can be seen, the insertion of a cornea implant into the cornea underneath a flap has considerable drawbacks and in particular results in a significant impairment of the stability of the cornea on account of the lamellar cut in the cornea for producing a flap. This impairment of the stability of the cornea is typically experienced in LASIK surgery, where a similar flap needs to be created.

Ring-shaped cornea implants are also used in conjunction with techniques envisaging a circular incision in the corneal surface. GB 2095119 A, for instance, describes such a circular incision from the corneal surface into the corneal tissue, into which a ring of approximately 8 mm in diameter is introduced for the purpose of flattening the central cornea, which leads to myopia correction. Two different ring geometries are described and reference is made to their size. A circular ring section with a thickness of approx. to 0.5 mm and a triangular ring section with an edge length of approx. 0.3 mm. The materials mentioned are essentially polymer plastics. The disadvantage of this method is the significant traumatisation of the tissue. After inserting the ring into the corneal tissue, for instance, the incision needs to be closed with a suture along the full length of the circumference as otherwise the ring could not be maintained in a stable position inside the cornea, and the stability of the cornea would be massively impaired. Without a suture, the extent of correction, i.e. the dioptres treated, would not be controllable. But even with a suture, the extent of correction can only be foreseen to a certain extent if the ring is rigid enough and only marginally deformable to withstand a potential pull of the tissue resulting from the suture.

WO 93/12735 A1 describes a variant of GB 2095119 A with a bio-compatible, annular cornea implant, which is also inserted into the corneal stroma through a circular incision in the corneal surface for the purpose of correcting the refractive power in the myopic eye. Said implant is a ring with a fixed, i.e. unchangeable diameter, a refractive index that does not deviate from that of the corneal tissue by more than 2% and may have the following dimensions: ring diameter approx. 2.4 mm to 12 mm, ring width approx. 0.2 mm to 4 mm and ring thickness approx. 0.005 to 0.2 mm. The ring has a convexly shaped front side and a flat back side. In this case, too, the traumatisation of the tissue when inserting the implant is considerable. Another major drawback when using the implant inside the cornea is the flat back side of the ring. Since the corneal surface is curved with a radius of approx. 8 mm, this leads to the fact that with the ring widths indicated the shape of the back side of the ring and the corresponding corneal cut inside the cornea pocket are in part considerably different from each other. Such a disproportionate geometry may, as frequently described in the literature, lead to massive accumulation of deposits of organic material along the interfaces, which may lead to vision impairment and undesirable cosmetic results. Moreover, this results in a highly uneven distribution of pressure on the tissue across the back face of the ring, which may induce pressure atrophies and tissue necrosis.

To avoid the disadvantages described above, methods have been developed where the respective cornea implant is inserted into a fully enclosed cornea pocket via a narrow, tunnel-shaped access. Since the inner tension of the cornea acts alongside the corneal lamellae, the formation of a basically enclosed cornea pocket does not reduce the bio-mechanically effective cross section for this tension and the bio-mechanical stability of the cornea is not impaired.

A suitable procedure and a suitable device for creating such a cornea pocket is, for instance, described in EP 1 620 049 B1, the content of which is therefore adopted in this application.

The creation of such a cornea pocket including a narrow, more or less tunnel-shaped access is, however, already known from US 2002/0055753 A1. After its insertion into the cornea pocket, the folded annular cornea implant is unfolded and placed in position. Although the insertion via a narrow tunnel works really well with these highly flexible, foldable cornea implants, this well-known procedure and the cornea implants inserted therewith have the decisive disadvantage that said implant has to be manually unfolded inside the pocket after insertion. However, a multitude of forces are effective inside the pocket after insertion of the cornea implant which prevent the cornea implant from unfolding itself, so that especially in the case of very flexible rings, there is a risk that the cornea implant does not resume its original predefined shape after implantation and astigmatisms or higher-order aberrations may be induced. Tedious, complicated manual manipulations therefore need to be taken into account after implantation to restore the initial ring form. But resuming the exact shape is often impossible and so the desirable correction of the refractive error may not be achieved. Moreover, the need for the cornea implant to be manually unfolded in the cornea pocket puts the cornea itself and above all the narrow, preferably tunnel-shaped access into the cornea pocket under unnecessary strain. In other words, a sufficiently flexible state-of-the-art cornea implant may facilitate the insertion into the cornea pocket via the narrow access, but simultaneously complicates the unfolding inside the cornea pocket.

The task of the present invention therefore is to create a cornea implant which has none of the drawbacks described above and may be used in a vision correction procedure, where a cornea implant is inserted into a cornea pocket via a narrow, preferably tunnel-shaped access.

DESCRIPTION OF THE INVENTION

According to the invention, this is achieved through the characterising features of claim 1.

The aim of the invention is that the annular cornea implant for inserting into a cornea pocket of the human eye via a narrow, preferably tunnel-shaped access, with the end shape of the cornea implant depending on the refractive error to be corrected, has a shape memory which is impressed on the basis of the geometry and/or material of the implant, and is designed in such a way that the deformability from a starting shape enables the insertion of the cornea implant into the cornea pocket via the tunnel-shaped access and the cornea implant has an adjustment force in die end shape thereof, which enables an essentially independent unfolding of the cornea implant in the cornea pocket.

According to a preferred embodiment of the invention, the starting shape and the end shape are identical.

To avoid an impairment of the biomechanical stability of the cornea as results when cutting a flap, the width of such a tunnel-shaped access to an otherwise closed cornea pocket should typically not exceed 5 mm, and ideally lie between 2 mm and 3 mm. A cornea implant according to the invention may therefore be inserted into the cornea pocket via a narrow access, the maximum width of which is below 5 mm, and preferably between 2 mm and 3 mm, to avoid an impairment of the biomechanical stability of the cornea as results when cutting a flap, without breaking or being altered in its shape (such as by permanent (irreversible) plastic deformation).

At the same time it is assured that the cornea implant, in addition to being sufficiently deformable, also has the ability to create an adequate adjustment force so as to safely unfold into a predefined form—its end shape—inside the cornea pocket after implantation. It unfolds more or less independently and automatically, without any additional or essential, additional manual interference.

A precondition for this is that on account of the impressed shape memory, one or several optional end shapes may be pre-programmed in the cornea implant according to the invention, and the latter, being either plastically or elastically deformed, assumes one of these end shapes either automatically or through activation by a trigger signal.

The shape memory is either impressed on the basis of a suitable chosen material, or on the basis of a special geometry of the cornea implant, or on the basis of a material-geometry combination.

The materials suited for insertion may be elastically or non-elastically deformable (plastic) materials. In elastic materials with a shape memory, the deformability and adjustment force mainly results from the elasticity of the material, such as PMMA (polymethyl methacrylate), silicone, etc. In non-elastic materials such as shape memory alloys, the adjustment force results, for example, from atomic forces which are released when one grid structure is spontaneously transformed into another.

Basically, there is a multitude of materials with a shape memory, which facilitate a shape memory of the cornea implants according to the invention. These include PMMA, polymers of EEMA or HEMA, or other acrylic materials, hydrogels, nylon, polycarbonate, polyethylene or other plastics, plastics with a temperature-dependent shape memory, shape memory alloys (e.g. based on Ni—Ti, Cu—Zn—Al, Cu—Al—Ni, etc.), suitable compounds of plastics and metals or non-metals (e.g. ceramics, semi-conductors, etc.), suitable compounds of metals and non-metals (e.g. ceramics, semi-conductors, etc.), or composite materials. Some of these materials, such as hydrogels, have already been used in cornea implants, but only the conditions under which they are applied and in particular the geometry of the cornea implant lead to the impression of the desirable shape memory.

It is important to assure that the desirable end shape can be achieved, by means of the adjustment force, from the intermediary shape into which the cornea implant needs to be deformed in order to be able to be inserted into the cornea pocket via the narrow access, irrespective of whether the starting shape and the end shape are identical or not.

The task according to the invention may, as mentioned before, also be solved exclusively or additionally by envisaging a special geometry of the cornea implant.

Therefore also known elastic materials may be used as cornea implantation body, which receive the desirable shape memory due to their geometrical design.

An exact fitting of the adjustment force is of vital importance because the cornea implant is only in its end shape suited to correct the respective refractive error. If the end shape cannot be achieved or is not exactly achieved, the correction of the refractive error is also inadequate.

After being implanted into the cornea pocket, the cornea implant is exposed to considerable forces that act against its unfolding, such as the frictional forces resulting from the pocket walls between which the cornea implant is positioned. This is further enhanced by forces resulting from the intrinsic tension of the cornea and the intraocular pressure.

The impression of a shape memory alone is therefore insufficient, and it must additionally be guaranteed that the—preprogrammed—end shape is achieved by means of an adjustment force that is suited to overcome the forces acting against the unfolding of the implant to obtain its end shape.

According to another preferred embodiment of the invention, the material suited for impressing the shape memory is a material with a shape memory that can be activated, preferably a material with an electrically, thermally, mechanically or magnetically activable shape memory.

This enables the cornea implant, once implanted, to be readjusted at any time, with the possibility that the activation may also lead to different end shapes.

When using materials with a thermally activable shape memory according to the invention, the cornea implant may also adopt its desirable end form after plastic deformation. In a preferable embodiment of the invention, this is achieved by the targeted use of shape memory alloys.

By using materials with an activable shape memory as cornea implant according to the invention, it is moreover possible that the inserted cornea implant having reached its end shape may further change its end shape even after implantation, for example, by being activated through an electric or magnetic field created from outside or by having an electric current pass through it.

The group of materials with shape memory according to the invention also includes those which may change their size, or elasticity, or plasticity in the wake of swelling or deswelling, such as by absorption or extraction of water. Such materials may include completely or incompletely hydrated plastics, such as HEMA or hydrogels.

There are also materials with a shape memory where the end shape can be activated and adjusted by mechanical signals (e.g. by using ultrasound or reducing the frictional forces inside the pocket) or by chemical signals (e.g. change in pH value).

According to an alternative embodiment of the invention, the materials with a shape memory are shape memory alloys, for example those based on Ni—Ti, Cu—Zn—Al and Cu—Al—Ni. According to a preferred embodiment, such cornea implants are wrapped in an inert, biocompatible protective layer.

To enable a particularly exact automatic unfolding inside the cornea pocket, there is yet another preferred embodiment of the invention, according to which the choice of a suited material and the respective adjustment to the geometrical form of the annular cornea implant assures that the deformability of the cornea implant is at least 25 percent in at least one outer dimension of the ring, preferably the ring diameter, and the cornea implant has an adjustment force (or restoring force) into the original ring form (or desired end shape) in the range of 0.001N to 1N, ideally between 0.01N and 0.5N, in at least one direction (the direction of deformation), but ideally in all directions.

A particularly preferable geometrical form of the annular cornea implant has proven to be a cornea implant shaped like a circular ring with an outer diameter ranging between 4 mm and 12 mm, a ring width between 0.4 mm and 1.5 mm, preferably 0.5 mm, and a ring height between 0.01 mm and 0.8 mm. To this end, the inner diameter of the ring should not lie within the pupil width to avoid the perception of disturbing effects at the border.

The front face of the cornea implant is preferably convex and the back face preferably concave. This assures that the pocket wall more or less flawlessly adheres to the cornea implant, with the front and back face of the ring seamlessly flowing into each other at the edges.

On account of the good deformability and sufficient adjustment force according to the invention, the cornea implant may also have the shape of a closed or split ring and still be inserted into the cornea pocket via the narrow access without difficulty. The shape of a closed ring guarantees that the cornea implant, after being implanted in the cornea pocket, resumes an annular, undistorted and stable ring form.

The cornea implant may have the form of a circular ring as its end shape for the correction of shortsightedness, or a non-circular ring form for the correction of other refractive errors, such as astigmatism in the case of an elliptic ring form.

Reference to additional preferred embodiments of the invention is made under the sub-claims listed below.

SHORT DESCRIPTION OF THE DRAWINGS

The following is a detailed description of the invention using examples of embodiments. The figures show the following:

FIG. 1 a sectional view of a cornea implant according to the invention

Figure 2:
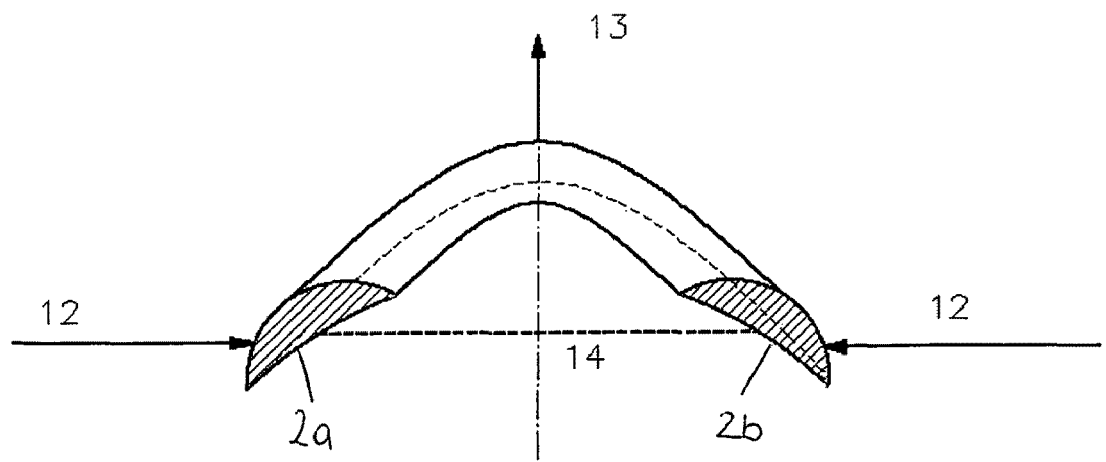
Figure 3:
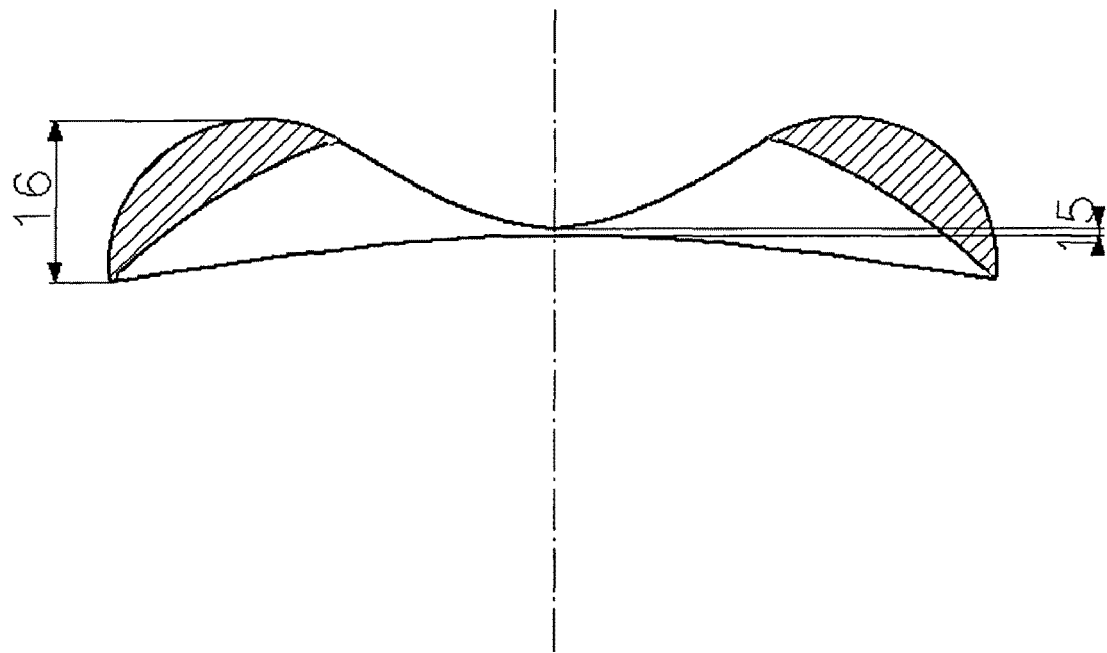
Figure 4:
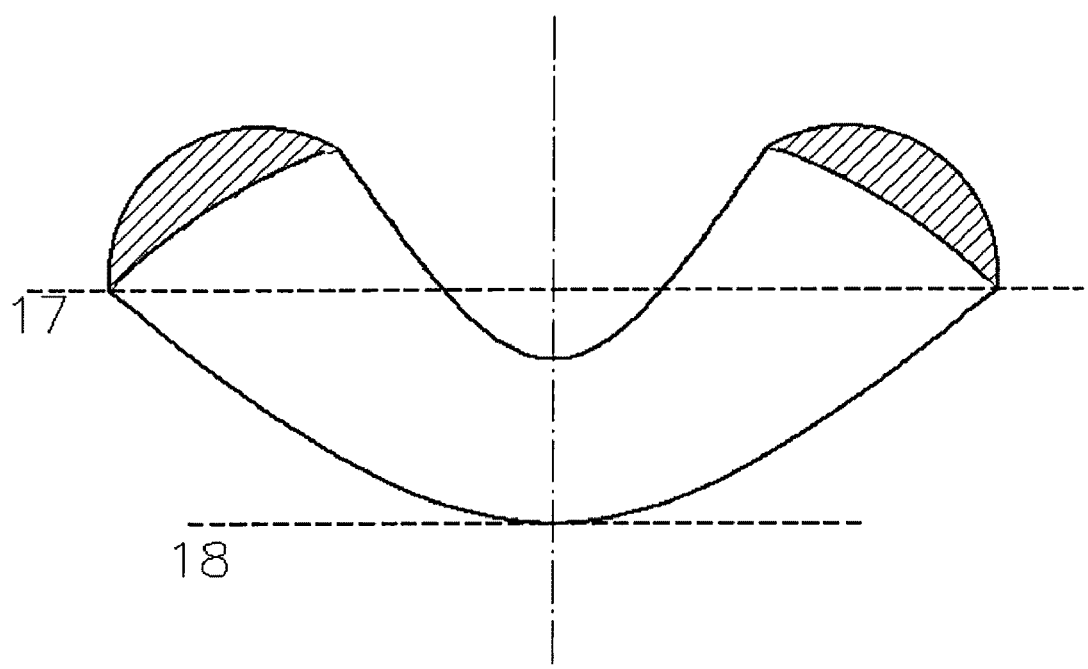
Figure 5A:
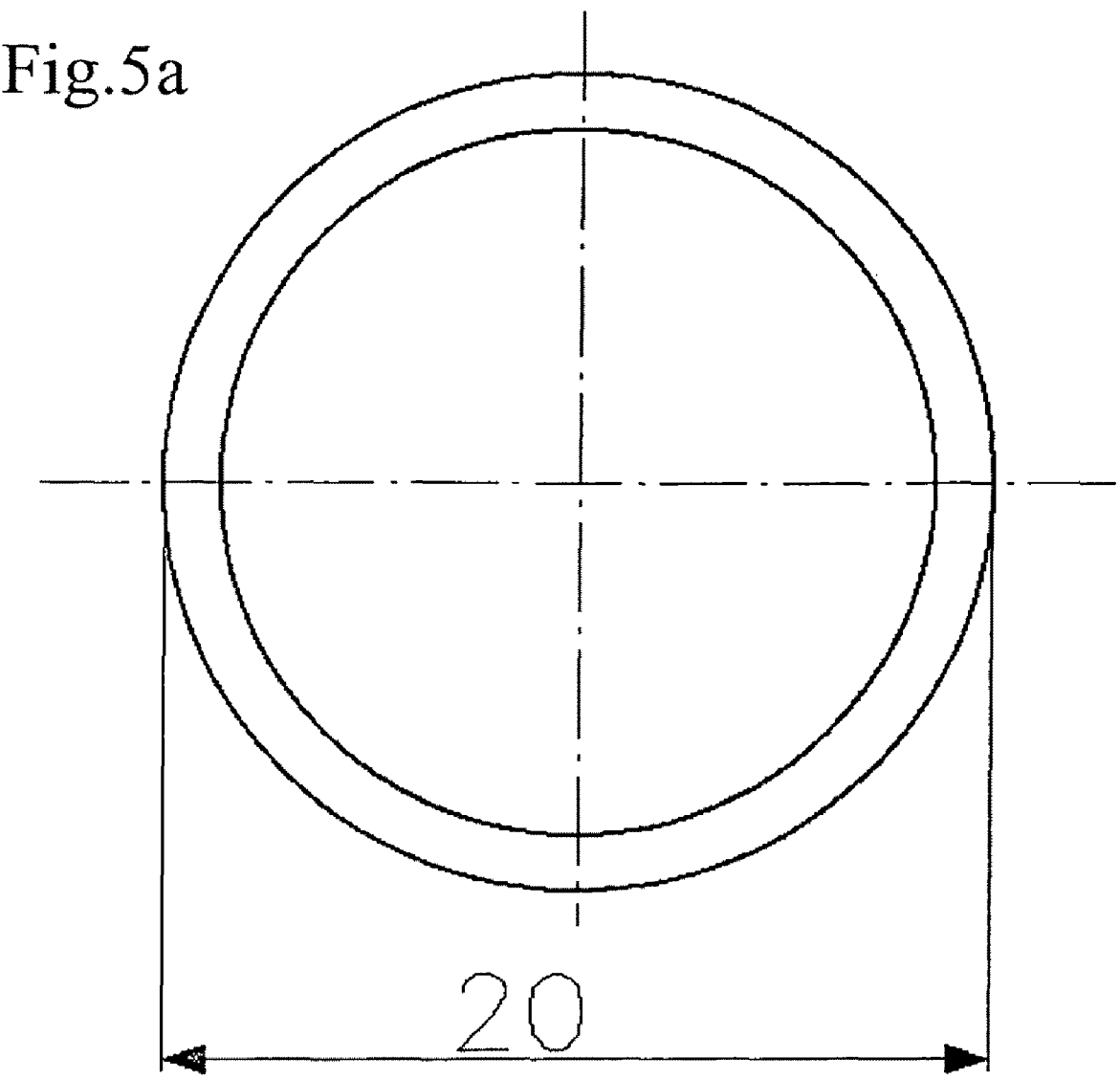
Figure 5B:
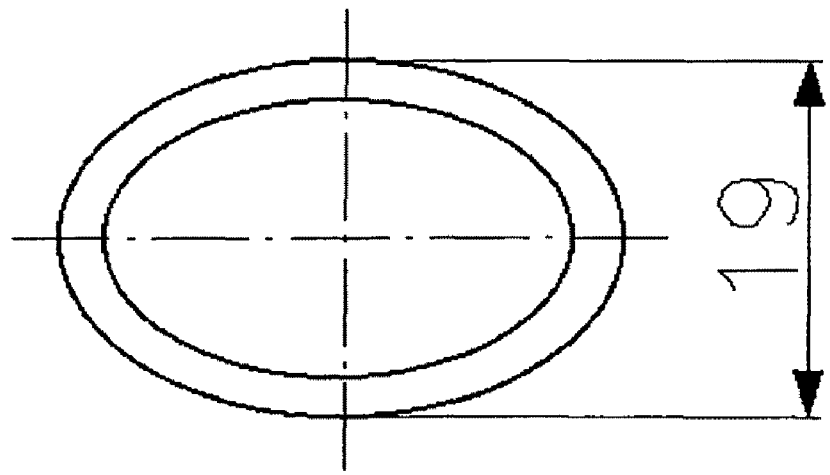
Figure 6A:
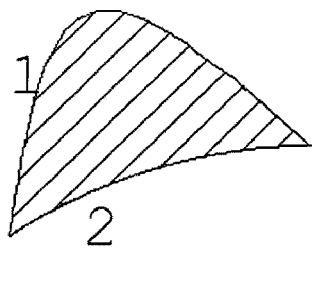
Figure 6F:
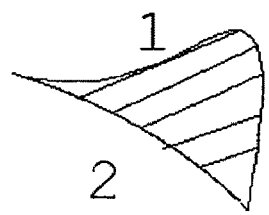
Figure 6B:
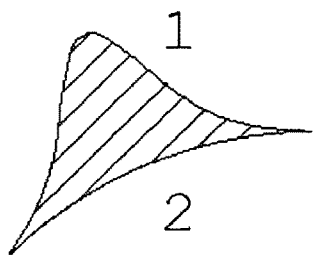
Figure 6G:
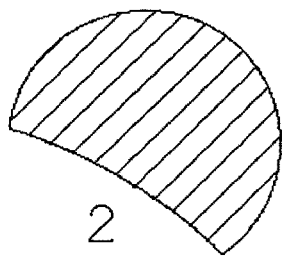
Figure 6C:
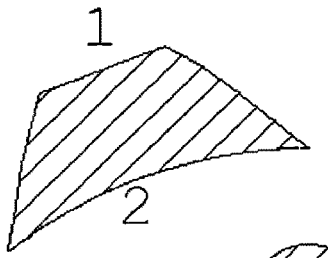
Figure 6H:
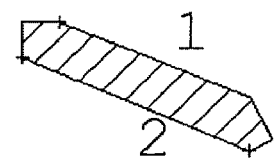
Figure 6D:
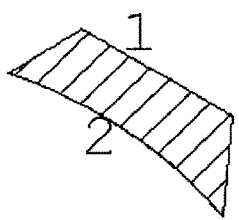
Figure 6I:
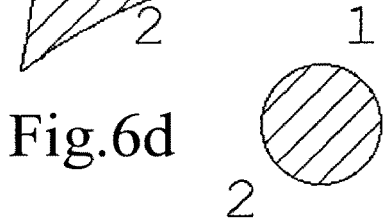
Figure 6E:
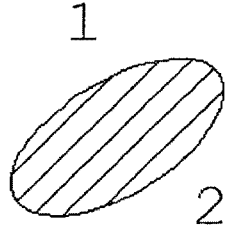
Figure 6J:
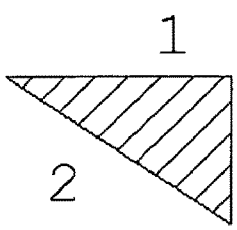
Figure 7A:
Figure 7B:
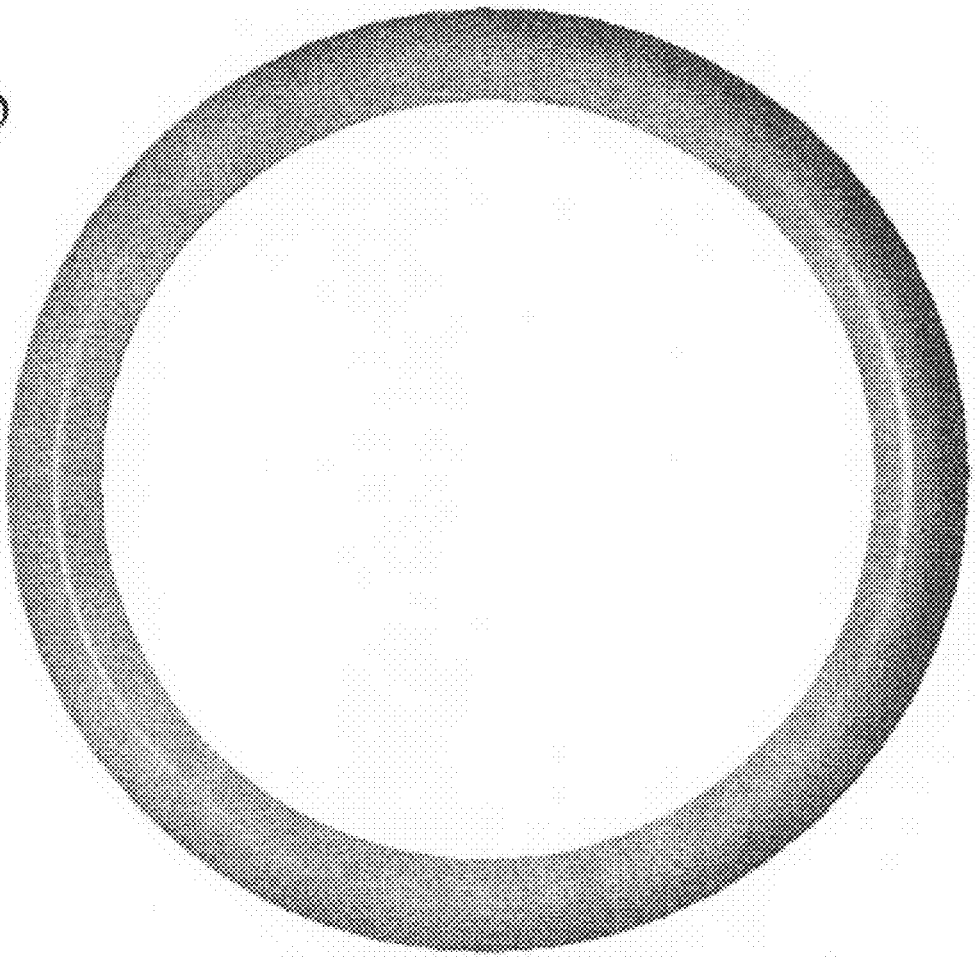
Figure 7C:
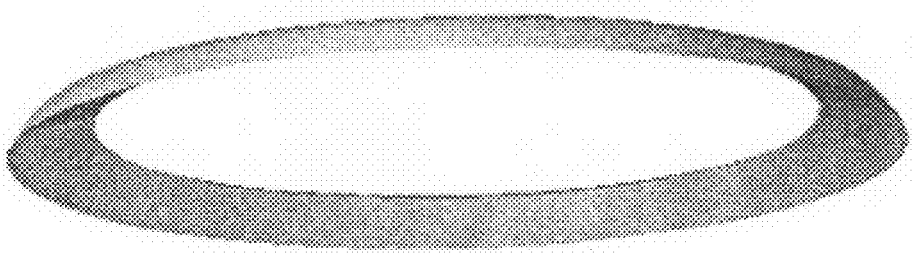
Figure 7D:
Figure 8A:
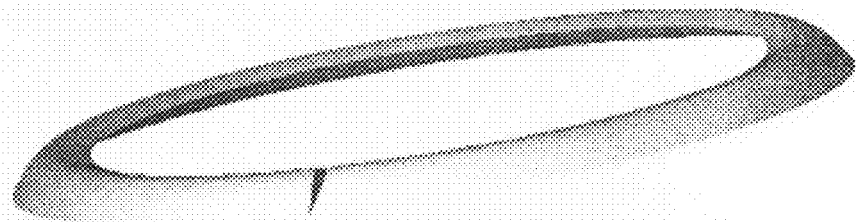
Figure 8B:
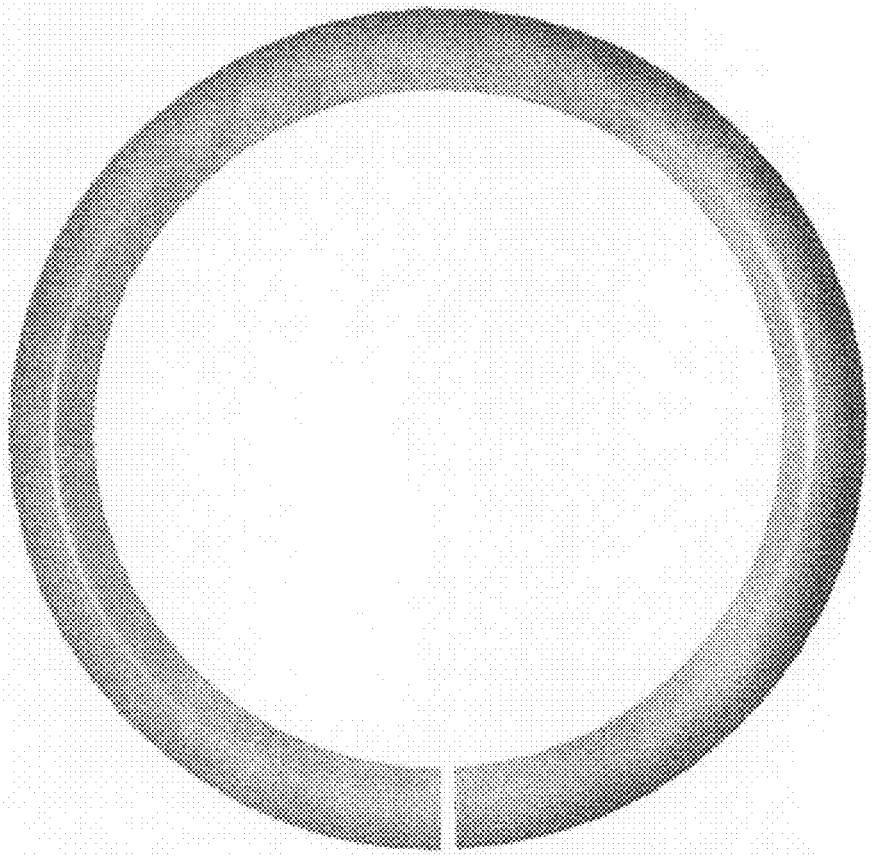
Figure 8C:
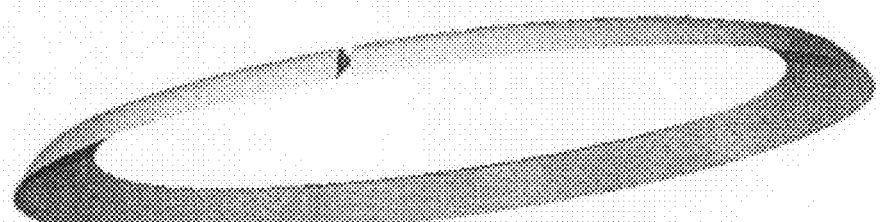
Figure 8D:
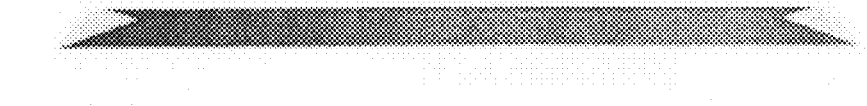
Figure 9A:
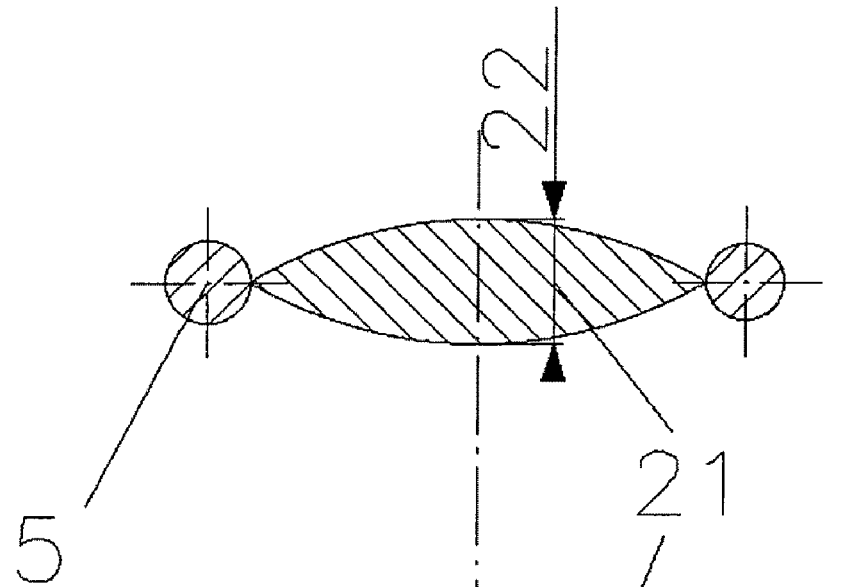
Figure 9B:
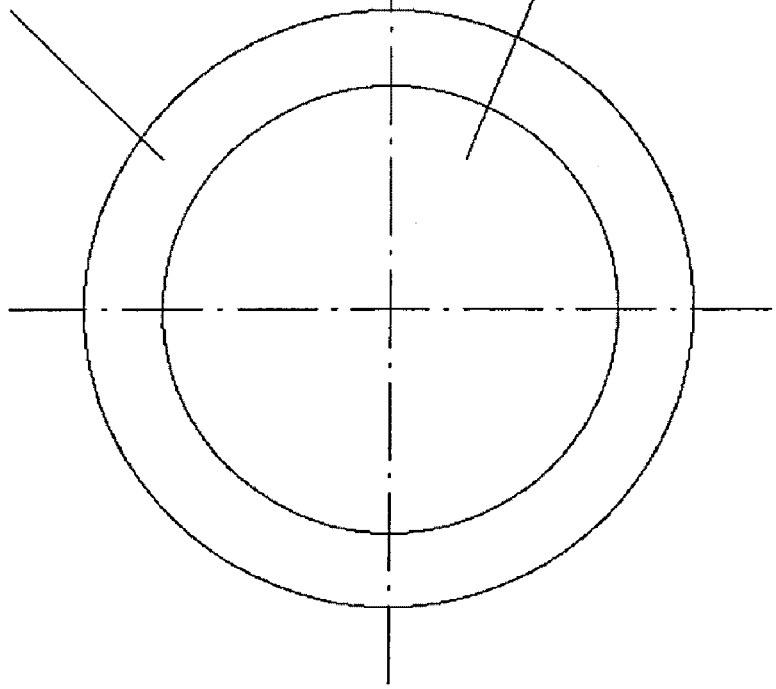
Figure 10:
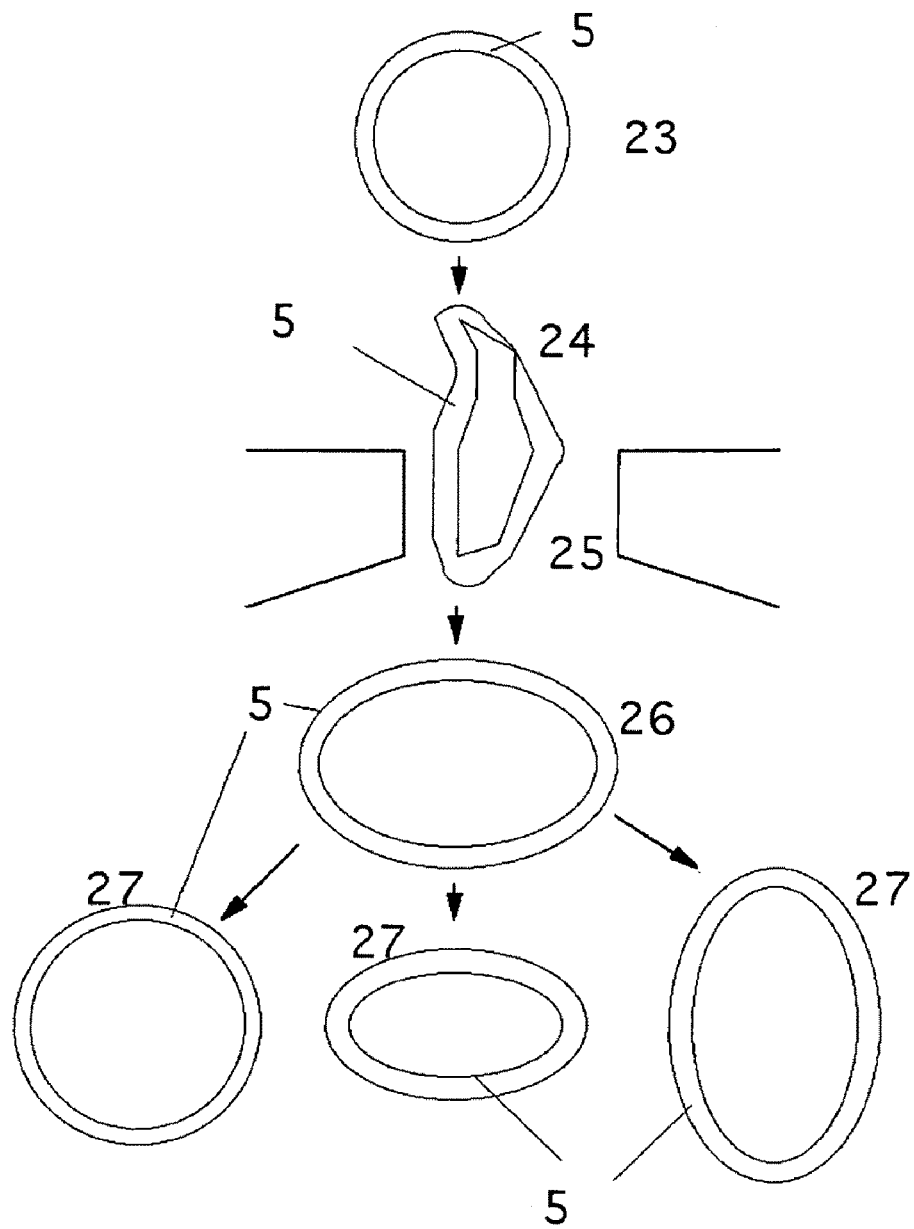

FIG. 2 a cornea implant according to the invention which has been deformed for the purpose of inserting it via a tunnel-shaped access FIG. 3 a cornea implant according to the invention with different annular cross sections along the circumference FIG. 4 a cornea implant according to the invention with a saddle-shaped ring geometry FIG. 5a a cornea implant according to the invention with an annular shape FIG. 5b a cornea implant according to the invention with a different annular shape FIG. 6a a cornea implant according to the invention with a first cross section FIG. 6b a cornea implant according to the invention with a second cross section FIG. 6c a cornea implant according to the invention with a third cross section FIG. 6d a cornea implant according to the invention with a fourth cross section FIG. 6e a cornea implant according to the invention with a fifth cross section FIG. 6f a cornea implant according to the invention with a sixth cross section FIG. 6g a cornea implant according to the invention with a seventh cross section FIG. 6h a cornea implant according to the invention with an eighth cross section FIG. 6i a cornea implant according to the invention with a ninth cross section FIG. 6j a cornea implant according to the invention with a tenth cross section FIG. 7a a front perspective view of a cornea implant according to the invention having the shape of a closed circular ring FIG. 7b a front view of a cornea implant according to the invention having the shape of a closed circular ring FIG. 7c a rear perspective view of a cornea implant according to the invention having the shape of a closed circular ring FIG. 7d an elevational view of a cornea implant according to the invention having the shape of a closed circular ring FIG. 8a a front perspective view of a cornea implant according to the invention having the shape of a split circular ring FIG. 8b a front view of a cornea implant according to the invention having the shape of a split circular ring FIG. 8c a rear perspective view of a cornea implant according to the invention having the shape of a split circular ring FIG. 8d an elevational view of a cornea implant according to the invention having the shape of a split circular ring FIG. 9a a cross section of an annular cornea implant according to the invention with a central lens body FIG. 9b a front view of the annular cornea implant with a central lens body shown in FIG. 9a FIG. 10 illustration of an implantation process where an annular cornea implant according to the invention is inserted into a cornea pocket via a narrow tunnel

WAYS TO EXECUTE THE INVENTION

As seen in FIG. 1, a cornea implant according to the invention comprises an annular ring body 5, which has a convex front face 1 and a concave back face 2. The concavity of the back face 2 may be spherical or aspherical, such as by approximation via several spherical curvatures. The centres of curvature 3 of the radii of curvature 10 of the two back face sections 2a, 2b are preferably arranged alongside the axis 4 of the cornea implant according to the invention. In aspherical back faces, several centres of curvature 3 are arranged alongside the axis 4, which corresponds to the optical axis.

Apart from allowing a perfect adjustment of the back face of the ring to the implantation bed and preventing the formation of deposits and pressure atrophies in the tissue, this also drastically increases the deformability of the rings, without reducing the adjustment force in the same way.

The outer diameter 6 of the cornea implant is preferably in the range of 4 mm to 12 mm, ideally between 5 mm and 9 mm. The inner diameter 11 is preferably in the range of 3 mm to 11 mm, ideally between 4 mm and 8 mm. The ring width 8 is ideally 0.5 mm, ought to be less than 1 mm to ensure a proper nutrient supply, and is preferably between 0.4 mm and 1.5 mm.

The ring height 9 is in the range of 0.01 mm to 0.8 mm, ideally between 0.1 mm and 0.4 mm.

The inner diameter 11 of the cornea implant should in any case be wider than the respective pupil width to avoid effects at the border which the patient may find disturbing.

The front and back faces 1 and 2 flow seamlessly into each other at the edges.

The back face 2 ideally follows the natural course of the corresponding pocket wall inside the cornea (local corneal radii minus pocket depth plus (or by) correction factor, which considers the deformation of the cornea resulting from the insertion into the pocket), so that the concave progression of the back face of the ring corresponds to a spherical or aspherical curvature, with radii 10 lying between 4 mm and 40 mm, preferably between 6 mm and 10 mm.

According to the invention, the cornea implant 5 has a shape memory which is impressed on the basis of its material and/or geometry and designed in such a way that the cornea implant has a deformability from a starting shape, which enables the insertion of the cornea implant into the cornea pocket via the narrow, preferably tunnel-shaped access with an inner width of less than 5 mm and concurrently has an adjustment force in the end shape thereof, which enables an essentially independent unfolding of the cornea implant in the cornea pocket.

The preferred materials for this purpose may include plastics such as PMMA, HEMA, silicone, polycarbonates, polyethylene or other polymer plastics or shape memory alloys.

FIG. 2 shows a cornea implant according to the invention, which is laterally compressed by force, as symbolised by the arrows 12, to be able to be inserted via the narrow access (not included) into a cornea pocket.

With respect to the elastic deformation of materials, the adjustment force is in general reciprocally proportionate to the deformability.

When using materials which are only elastically deformable within a very narrow deformation range (e.g. PMMA), it is essential to give the cornea implant a special shape by which it becomes sufficiently deformable yet also retains its restoring force.

In the case of a cornea implant as illustrated in FIG. 2, this is achieved by the special contour line of the back face 2 towards the ring center, where the centers of curvature 3 of the radii 10 are arranged along the axis 4, thus not only achieving a simple oval shape, but a saddle-shaped object as a part of the ring deviates from the ring level 14 into the third dimension 13 when being deformed (compression). This generates an additional degree of freedom, which considerably increases the deformability without essentially reducing the adjustment force.

According to the invention, the deformability must be at least 25 percent of a typical annular dimension and the cornea implant has an adjustment force into the original ring form in the range of 0.001N to 1N, ideally between 0.01N and 0.5N.

A typical ring dimension in a circular cornea implant, for instance, is the ring diameter 20, whereas in an elliptic cornea implant, for instance, it is the minor axis 19 (FIG. 5).

In the embodiments according to FIG. 1 and FIG. 2 it is even possible to deform a ring made of PMMA (a material that is difficult to deform and easily breaks when being deformed), which has an outer diameter 6 of 5 mm, a ring width 8 of 0.5 mm and a ring height 8 of 0.25 mm as well as a radius of curvature 10 of 8 mm, by approximately 50% of its diameter, yet assuring that it does not break and retains a sufficient adjustment force to freely and independently resume its original ring geometry after being implanted in the cornea pocket against the forces resisting its unfolding. In this case, the impression of the shape memory results exclusively from a special geometry, whilst the choice of material is of no relevance.

To enable an exact fitting of the adjustment force, the cornea implant may have different ring cross sections 15,16 along the circumference, as is illustrated in FIG. 3.

When it has the form of a "saddle", the basic edges 17, 18 along the ring circumference are not on the same level, as can be seen in FIG. 4.

Depending on the refractive error to be corrected, the cornea implant 5 according to the invention may have all sorts of different cross sections, as can be seen in FIG. 6.

An exact attuning of the material and geometry of the cornea implant 5 to each other assures that the cornea implant may unfold independently inside the cornea pocket after insertion.

The respective material may be a material with a shape memory that can be activated, preferably a material that can be electrically, thermally, mechanically or magnetically activated, such as shape memory alloys.

The trigger signal for such activation may for instance be the temperature, so that the cornea implant according to the invention is sufficiently deformable in a cooled-down condition for inserting it into the cornea pocket via the narrow, preferably tunnel-shaped access. The cornea implant warms up inside the cornea pocket until reaching a certain trigger temperature, where the cornea implant resumes its end shape or, being exposed to an adequate adjustment force between 0.001N and 1N, ideally between 0.01N and 0.5N, approaches its end shape. Since the temperature inside the cornea may not be sufficient to achieve the trigger temperature, heat may also be introduced from outside the eye.

In the case of a material with a shape memory that can be magnetically or electrically activated, the material may, for instance, contain elements based on, or entirely consist of, Ni—Mn—Ga. After the successful implantation in the cornea pocket according to the invention, an adjustment from one end shape into another end shape may be achieved by inducing a voltage to the implant or exposing it to an electric or magnetic field. This even enables a posterior fine-tuning or adjustment of dioptres, such as would be necessary if the dioptres of the eye were to change again over time, without the need to replace the cornea implant.

In principle, different trigger signals may be used to activate the shape memory, including mechanical or chemical trigger signals. So when using certain materials, such as those appropriate due to their elastic deformability, the assumption of a defined end shape can be fostered by applying ultrasound or exerting pressure on the cornea implant or the bed of the implant. Moreover, by changing the degree of swelling of the implant, such as by adding or extracting liquid, the assumption of a shape may be facilitated or a respective activation energy required for obtaining a certain shape may be overcome. Moreover, such a trigger signal may also be released by an intentional pH value change in the tissue surrounding the implant or in the cornea implant proper.

Typical materials with a shape memory that can be activated are for instance polymer metals, ionic polymer-metal composites, IMPC, electroactive polymers (e.g. electronic or ionic EAP materials) such as polyacrylonitril (PAN), ceramics or electroactive ceramics, suited conductor or semi-conductor plastics, ionic polymeric conductor composites, IPCC, and magnetic shape memory elements such as those based on NiMnGa or Ni2MnGa.

Shape memory alloys may be alloys based on Ni—Ti, Cu—Zn—Al, Cu—Al—Ni and other materials. Plastics with a temperature-dependent shape memory as well as shape memory alloys may be easily deformed (in particular also by plastic deformation) preferably below a specific transformation temperature, but resume a predefined shape above this transition temperature. In this manner, changing the temperature of the folded cornea implant in its intermediate shape may help to achieve its unfolding into the desired shape after being inserted into the stromal implantation bed.

Shape memory alloys are characterised by a martensitic phase transition (second-order phase transition), where the material changes its crystalline structure when a specific transformation temperature is exceeded and assumes a predefined shape. This is an atomic and not a molecular phenomenon, such as in elastic deformation, where mostly polymer molecules are deformed. When a transformation temperature is exceeded, in fact, the atoms of the material spontaneously adopt an entirely different order. Although some shape memory alloys are biocompatible, shape memory alloys may be coated with silicone or any other inert, biocompatible materials (e.g. plastics) to assure that the tissue is not directly exposed to the alloy and thus cannot suffer any damage. Such cornea implants are also able to create pressure inside the tissue, such as when pressure is exerted against the cutting edges, which may additionally result in any kind of deformation of the corneal surface. Such cornea implants may have any shape, in particular they may be open or closed, annular (see FIGS. 7 and 8), elliptic, saddle-shaped with one or more saddles, spiral-shaped, single- or multi-threaded, curved or straight, etc. The implants may or may not have a plastic coating. They may be continuous or segmented. They may be furnished with electrical contact elements. The majority of such elements are also suited for implantation into circular tunnels.

FIG. 9 shows an annular cornea implant with a central implantation body 21 according to the invention.

When correcting farsightedness, the central corneal radius needs to be reduced. This is why a central implantation body (lens) 21 needs to be chosen where the central thickness is higher than the peripheral thickness, whereas the aforementioned criteria related to the material of an annular cornea implant without a central implantation body invariably also apply in this case. In particular, a cornea implant is recommended which is at least partly made of a material with a shape memory or one that can be fine-tuned.

In this case, a central, possibly deformable lens 21, preferably one made of an elastic, transparent, biocompatible material, is enclosed by a ring body 5 with a shape memory. Because of the central lens and the surrounding ring being connected with each other, the lens may be inserted into the cornea pocket together with the ring and unfolded inside the pocket with the help of the ring, according to the invention. This may, for example, be achieved through elastic forces or through the application of a certain temperature or an electric voltage or an electric or magnetic field. The central lens 21 and the ring 5 may be connected with each other in any way, such as by being welded together, by being wrapped up together in the same foil, by being glued together, by melting the ring into the lens, or by integrating the ring into the lens in any way. The central lens body 21 may, for instance, consist of hydrogel, HEMA, polyethylene, or any other polymer or non-polymer plastic. It is essential that the lens body is sufficiently permeable to oxygen and/or nutrients. Moreover, it can be elastic or non-elastic. The refractive index may be of any dimension whatsoever. The lens body 21 itself may also contain a shape memory. Embodiments as for an annular cornea implant without a central lens body 21 also apply without restrictions to annular cornea implants with a central lens body 21.

The ring body 5 may, in particular, be produced from any of the materials described above, including materials where the shape memory can be thermally, electrically or magnetically activated. This allows, for example, to use an electrically or magnetically readjustable ring body (as described elsewhere herein) for changing the tension and thus the central thickness (mean thickness) 22 of the elastic lens body 21, thereby influencing the impact of the latter in correcting the refractive error of the eye. By choosing an appropriate geometry for the central lens body 21, such as a diffractive or refractive bifocal or multifocal lens, also age-related farsightedness (presbyopia) may be corrected. It may, for instance, be designed as a Fresnel lens body. It may consist of a partly or fully non-transparent material. It may also be designed as a lens body that is not dioptrically effective (e.g. without a central thickening 22). Moreover, if made of a non-transparent (e.g. black) material, it may be effective by producing an image through a single slot or multiple slots, or a single hole or multiple holes (i.e. holes that are arranged in a certain way to achieve a diffractive effect). These holes, due to their arrangement, may have a diffractive effect or, in case of only one hole, a stenopeic effect. However, these holes need not be physical holes, but may also be transparent spots in an otherwise non-transparent medium to achieve this effect. The statements made, in particular those relating to (open) ring-shaped structures or segments, not only apply on the basis of the implantation pocket described herein, but also have validity with respect to other implantation pockets, especially for complete or segmented annular pockets, such as those used for implanting Intacs.

For the correction of astigmatism, rings (open, closed, split or segmented) or central bodies with an asymmetrical shape or cross section are needed. Myopic astigmatism is therefore most easily corrected by using a round implant with different cross sections along the main axes, or with a homogeneous cross section but preferably elliptic ring shape, or a combination of both. The same applies to hyperopic astigmatism, with the difference that not the ring but the central body (lens) is asymmetrical, and that this asymmetry is preferably impressed on the body by one of the aforementioned materials and/or shapes. In particular, the central radii of the two main sections of the astigmatic implantation body are different.

FIG. 10 illustrates the implantation procedure of an annular cornea implant, according to the invention, being inserted into a cornea pocket via a narrow tunnel. To this end, an annular cornea implant 5 with any type of starting shape 23, but preferably one that corresponds to the end shape 26 or 27, is deformed so as to adopt an intermediate shape 24 for inserting into the cornea pocket via a tunnel 25. Subsequently, through the shape memory according to the invention which is impressed on the implant 5, the intermediate shape 24 is changed into a predefined shape 26 (end shape) inside the cornea pocket. This shape preferably corresponds to the initial starting shape 23, but may also be different. This change of shape may take place automatically or may be triggered directly or indirectly via an appropriate trigger signal. Such a trigger signal is ideally a temperature increase in the implant exceeding a certain transformation temperature. Subsequently, the implant may, in certain cases, change from an end shape 26 into another end shape 27. This change from one end shape 26 into another end shape 27 is ideally triggered by electric or magnetic signals. The end shape 27 may, in particular, be determined by the electric or magnetic field strength applied or by the electric current through the implant 5.

It needs to be stressed that each feature of an embodiment can be combined with any feature of another embodiment, to obtain a new embodiment.

The invention claimed is:

1. Annular cornea implant for inserting into a cornea pocket of the human eye via a narrow access to the cornea pocket to correct a refractive error of the eye, comprising:
   i. a starting shape comprising a circular or elliptical ring body having a ring width and a ring height, said ring body further comprising a plurality of starting dimensions disabling insertion of the cornea implant into the cornea pocket via the narrow access, said plurality of starting dimensions comprising a starting shape outer dimension selected from the group consisting of a diameter ranging from 4 mm to 12 mm and a minor axis ranging from 4 mm to 12 mm,
   ii. a deformability into an intermediate shape, said intermediate shape being generated from the starting shape by laterally compressing the cornea implant in such a way to form intermediate dimensions comprising an intermediate shape outer dimension smaller than the starting shape outer dimension to enable the insertion of the implant into the cornea pocket via the narrow access, and
   iii. an adjustment force which enables independent unfolding from the intermediate shape into an end shape to be adopted after inserting the cornea implant into the cornea pocket via the narrow access, the end shape comprising ending dimensions comprising an end shape outer dimension larger than the intermediate shape outer dimension,
   wherein the ring body has an impressed shape memory from at least one of a material of the ring body and a geometry of the ring body such that in the starting shape the ring body is disposed in a ring level extending in first and second dimensions, in the intermediate shape a part of the ring body is deviated from the ring level into a third dimension orthogonal to at least one component of a compression force applied to the ring body to form the intermediate shape, and after inserting the cornea implant into the cornea pocket via the narrow access the end shape is adopted as a result of independent unfolding of the ring body caused by the adjustment force; and
   wherein the annular cornea implant comprises an intracorneal implant.

2. Annular cornea implant for inserting into a cornea pocket in the human eye via a narrow access to the pocket according to claim 1, wherein the starting shape and the end shape are substantially identical.

3. Annular cornea implant for inserting into a cornea pocket in the human eye via a narrow access to the pocket according to claim 1, wherein the intermediate shape outer dimension is at least 25 percent smaller than the starting shape outer dimension.

4. Annular cornea implant for inserting into a cornea pocket in the human eye via a narrow access to the pocket according to claim 3, wherein the adjustment force is in a range of 0.001 N to 1 N.

5. Annular cornea implant for inserting into a cornea pocket in the human eye via a narrow access to the pocket according to claim 3, wherein the ring body comprises a rigid material.

6. Annular cornea implant for inserting into a cornea pocket in the human eye via a narrow access to the pocket according to claim 1, wherein the ring body comprises exterior front and back faces, the front face being convex and the back face being concave.

7. Annular cornea implant for inserting into a cornea pocket in the human eye via a narrow access to the pocket according to claim 1, wherein the starting shape is a closed ring.

8. Annular cornea implant for inserting into a cornea pocket in the human eye via a narrow access to the pocket according to claim 7, wherein the ring body comprises exterior front and back faces, the front face being convex and the back face being concave.

9. Annular cornea implant for inserting into a cornea pocket in the human eye via a narrow access to the pocket according to claim 4, wherein the intermediate shape outer dimension is at least 25 percent smaller than at least one of the diameter, the ring width, and the ring height.

10. Annular cornea implant for inserting into a cornea pocket in the human eye via a narrow access to the pocket according to claim 7, wherein the ring body comprises a rigid material.

11. Annular cornea implant for inserting into a cornea pocket in the human eye via a narrow access to the pocket according to claim 1, wherein the ring width and the ring height vary circumferentially along the ring body.

12. Annular cornea implant for inserting into a cornea pocket in the human eye via a narrow access to the pocket according to claim 1, further comprising a central body of at least partial transparency arranged within an inner diameter of the ring body.

13. Annular cornea implant for inserting into a cornea pocket in the human eye via a narrow access to the pocket according to claim 1, wherein the part of the ring body deviated from the ring level comprises a limited range of a circumferential portion of the ring body, said circumferential portion having a cross-sectional area entirely deformed into the third dimension.

14. Annular cornea implant for inserting into a cornea pocket in the human eye via a narrow access to the pocket according to claim 1, wherein the ring body comprises a hydrated or partially hydrated material.

15. Annular cornea implant for inserting into a cornea pocket in the human eye via a narrow access to the pocket according to claim 1, wherein the intermediate shape outer dimension is at least 25 percent smaller than at least one of the diameter, the ring width, and the ring height.

16. Annular cornea implant for inserting into a cornea pocket in the human eye via a narrow access to the pocket according to claim 1, wherein the adjustment force is in a range of 0.001 N to 1 N.

17. Annular cornea implant for inserting into a cornea pocket in the human eye via a narrow access to the pocket according to claim 1, wherein the ring body comprises a rigid material.

18. Annular cornea implant for inserting into a cornea pocket in the human eye via a narrow access to the pocket according to claim 17, wherein the rigid material is poly (methylmethacrylate).

19. Annular cornea implant for inserting into a cornea pocket in the human eye via a narrow access to the pocket according to claim 1, wherein the intermediate shape is a saddle-shape.

* * * * *

UNITED STATES PATENT AND TRADEMARK OFFICE
CERTIFICATE OF CORRECTION

Page 1 of 1

PATENT NO.         : 8,092,526 B2
APPLICATION NO.    : 12/224966
DATED              : January 10, 2012
INVENTOR(S)        : Daxer It is certified that error appears in the above-identified patent and that said Letters Patent is hereby corrected as shown below:

In particular, on the Title page, item [86], please change the § 371 (c)(1), (2), (4) Date from "September 9, 2008" to correctly read: --September 10, 2008--.

In Column 13, line 12 (Line 3 of Claim 9) please change "claim 4" to read: --claim 7--.

Signed and Sealed this
Twentieth Day of March, 2012

David J. Kappos
*Director of the United States Patent and Trademark Office*